US011808701B2

(12) United States Patent
Schwartz et al.

(10) Patent No.: US 11,808,701 B2
(45) Date of Patent: Nov. 7, 2023

(54) SYSTEMS AND METHODS FOR IDENTIFYING SEQUENCE INFORMATION FROM SINGLE NUCLEIC ACID MOLECULE MEASUREMENTS

(71) Applicant: Wisconsin Alumni Research Foundation, Madison, WI (US)

(72) Inventors: David Charles Schwartz, Madison, WI (US); Subhrangshu Nandi, Madison, WI (US); Michael Abbott Newton, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 535 days.

(21) Appl. No.: 16/769,883

(22) PCT Filed: Dec. 4, 2018

(86) PCT No.: PCT/US2018/063785
§ 371 (c)(1),
(2) Date: Jun. 4, 2020

(87) PCT Pub. No.: WO2019/113024
PCT Pub. Date: Jun. 13, 2019

(65) Prior Publication Data
US 2021/0310055 A1    Oct. 7, 2021

Related U.S. Application Data

(60) Provisional application No. 62/594,385, filed on Dec. 4, 2017.

(51) Int. Cl.
*G06K 9/00* (2022.01)
*G01N 21/64* (2006.01)
(Continued)

(52) U.S. Cl.
CPC ....... *G01N 21/6428* (2013.01); *C12Q 1/6818* (2013.01); *G01N 21/6458* (2013.01);
(Continued)

(58) Field of Classification Search
CPC ........ G16H 50/20; G16H 10/40; G16H 50/30; G16H 50/70; G16H 15/00; G16H 20/10;
(Continued)

(56) References Cited

U.S. PATENT DOCUMENTS 7,960,105 B2    6/2011  Schwartz
2004/0214211 A1  10/2004  Gilmanshin et al.
(Continued)

FOREIGN PATENT DOCUMENTS

WO    2016036647 A1    3/2016
WO    2017009710 A2    1/2017

OTHER PUBLICATIONS

Gupta et al., Optical Mapping and Nanocoding Approaches to Whole-Genome Analysis, Microfluid Nanofluid, 2016, 20:44, 14 pages.
(Continued)

*Primary Examiner* — Alex Kok S Liew
(74) *Attorney, Agent, or Firm* — Quarles & Brady LLP

(57) ABSTRACT

Systems and methods for identifying sequence information from measurements made on single nucleic acid molecules are disclosed. The systems and methods can include binding portions of nucleic acid molecules with marker molecules, such as fluorescent molecules and/or intercalating molecules. The marker molecules provide a detectable signal that includes information about the underlying genomic information of the location on the nucleic acid molecule where a given marker molecule is bound. A profile of the detectable signal along a position of the nucleic acid is acquired for multiple different nucleic acid molecules. The
(Continued)

PRIMR algorithm processes the data to provide a consensus profile from which a consensus underlying genomic information can be determined.

48 Claims, 4 Drawing Sheets

(51) Int. Cl.
    *G16B 30/00*     (2019.01)
    *C12Q 1/6818*     (2018.01)
    *G02B 21/16*     (2006.01)
    *G02B 21/36*     (2006.01)
    *G06V 20/69*     (2022.01)

(52) U.S. Cl.
    CPC ........... *G02B 21/16* (2013.01); *G02B 21/365* (2013.01); *G06V 20/693* (2022.01); *G06V 20/695* (2022.01); *G06V 20/698* (2022.01); *G16B 30/00* (2019.02); *G01N 2021/6439* (2013.01); *G06V 2201/03* (2022.01)

(58) Field of Classification Search
    CPC ......... G06T 7/0012; G06T 2207/10064; G06T 2207/30024; G06T 2207/30096; G06T 2207/10056; G06T 2207/20036; G06T 2207/20076
    See application file for complete search history.

(56) References Cited

U.S. PATENT DOCUMENTS

| | | | |
|---|---|---|---|
| 2009/0104611 A1 | 4/2009 | Schwartz et al. | |
| 2010/0235105 A1* | 9/2010 | Volkov | C12Q 1/6813 702/19 |
| 2010/0304990 A1* | 12/2010 | Gifford | C12Q 1/6827 435/6.15 |
| 2011/0096955 A1* | 4/2011 | Voloshynovskiy | G07F 7/0813 382/103 |
| 2014/0140607 A1* | 5/2014 | Erjefalt | G06V 20/695 382/133 |
| 2017/0018084 A1* | 1/2017 | Mah | G06T 7/0016 |

OTHER PUBLICATIONS

Hastie et al., Rapid Genome Mapping in Nanochannel Arrays for Highly Complete and Accurate De Novo Sequence Assembly of the Complex Aegilops Tauschii Genome, PLOS One, 2013, 8(2):e55864, pp. 1-10.
Reslewic et al., Whole-Genome Shotgun Optical Mapping of Rhodospirillum Rubrum, Applied and Environmental Microbiology, 2005, 71(9):5511-5522.
Schwartz et al., Ordered Restriction Maps of *Saccharomyces cerevisiae* Chromosomes Constructed by Optical Mapping, Science, 1993, 262:110-114.
European Patent Office, Extended Search Report, Application No. 18885770, dated Nov. 25, 2021, 16 pages.
Breiman, L. 1996. Bagging predictors. Machine learning 24(2):123-140.
Breiman, L. 2001. Random forests. Machine learning 45(1):5-32.
Brock, G. et al. 2011. clvalid, an r package for cluster validation. Journal of Statistical Software.
Buhlmann P. et al. 2003. Boosting with the l 2 loss: regression and classification. Journal of the American Statistical Association 98(462):324-339.
Chen, X. et al. 2012. Random forests for genomic data analysis. Genomics 99(6):323-329.
Dimalanta, E.T., et al. A microfluidic system for large DNA molecule arrays. Anal Chem, 2004. 76(18): p. 5293-301.

Febrero, M. et al. 2008. Outlier detection in functional data by depth measures, with application to identify abnormal hox levels. Environmetrics 19(4):331-345.
Febrero-Bande, M, et al. 2012. fda.usc: Functional data analysis and utilities for statistical computing (fda.usc). R package version 0.9 7. Accessed online at https://web.archive.org/web/20130706035232/ http://cran.r-project.org/web/packages/fda.usc/fda.usc.pdf.
Febrero-Bande, M. et al. 2012. Statistical computing in functional data analysis: the r package fda. usc. Journal of Statistical Software 51(4):1-28.
Friedman, J. H. 2001. Greedy function approximation: a gradient boosting machine. Annals of statistics 1189-1232.
Gupta, A., et al. Single-molecule analysis reveals widespread structural variation in multiple myeloma. Proc Natl Acad Sci U S A, 2015. 112(25): p. 7689-94.
International Searching Authority. International Search Report and Written Opinion for application PCT/US2018/063785. dated Feb. 6, 2019. 15 pages.
Jo, K., et al. 2007. A single-molecule barcoding system using nanoslits for dna analysis. Proceedings of the National Academy of Sciences 104(8):2673-2678.
Kent, W.J., et al, The human genome browser at UCSC. Genome Res, 2002. 12(6): p. 996-1006.
Kounovsky-Shafer, K. L. et al. "Electrostatic confinement and manipulation of DNA molecules for genome analysis." Proceedings of the National Academy of Sciences 114.51 (2017): 13400-13405.
Kounovsky-Shafer, K. L. et al. 2013. Presentation of large dna molecules for analysis as nanoconfined dumbbells. Macromolecules 46(20):8356-8368.
Lai, Z., et al, A shotgun optical map of the entire Plasmodium falciparum genome. Nat Genet, 1999. 23(3): p. 309-13.
Lee, S., et al. (2016). DNA binding fluorescent proteins for the direct visualization of large DNA molecules. Nucleic Acids Research, 44(1), e6. doi:10.1093/nar/gkv834.
Liaw, A. et al. 2002. Classification and regression by randomforest. R news 2(3):18-22.
Lin, J., et al al. Whole-genome shotgun optical mapping of Deinococcus radiodurans. Science, 1999. 285(5433): p. 1558-62.
Mitra, R.D., et al. Fluorescent in situ sequencing on polymerase colonies. Anal Biochem, 2003. 320(1): p. 55-65.
Nandi, S. "Statistical Learning Methods for Fluoroscanning", doctoral dissertation, University of Wisconsin-Madison. 2017.
Netzel, T.L., et al. Base-content dependence of emission enhancements, quantum yields, and lifetimes for cyanine dyes bound to double-strand DNA: Photophysical properties of monomeric and bichromophoric DNA stains. Journal of Physical Chemistry, 1995. 99(51): p. 17936-17947.
Nilsson, A.N., et al. Competitive binding-based optical DNA mapping for fast identification of bacteria—multi-ligand transfer matrix theory and experimental applications on *Escherichia coli*. Nucleic Acids Res, 2014. 42(15): p. e118.
Noble, C., et al, A fast and scalable kymograph alignment algorithm for nanochannel-based optical DNA mappings. PLOS One, 2015. 10(4): p. e0121905.
Reisner, W., et al. Single-molecule denaturation mapping of DNA in nanofluidic channels. Proc Natl Acad Sci U S A, 2010. 107(30): p. 13294-9.
Ridgeway, G., et al. 2006. gbm: Generalized boosted regression models. R package version 1(3):55. Accessed online at https://web. archive.org/web/20170715064502/https://cran.r-project.org/web/ packages/gbm/gbm.pdf.
Rye, H.S., et al. Stable fluorescent complexes of double-stranded DNA with bis-intercalating asymmetric cyanine dyes: properties and applications. Nucleic Acids Res, 1992. 20(11): p. 2803-12.
Sarkar, D., et al. Statistical significance of optical map alignments. J Comput Biol, 2012. 19(5): p. 478-92.
Sheats, J. et al. "Measurements of DNA barcode label separations in nanochannels from time-series data." Biomicrofluidics 9.6 (2015): 064119.
Stahel, W. et al. 2009. Package robustx. Electronic file available at http://cran.r-project.org/web/packages/robustX/index.html Accessed Feb. 25, 2021.

(56) References Cited

OTHER PUBLICATIONS

Stavropoulos, D.J., et al, Whole Genome Sequencing Expands Diagnostic Utility and Improves Clinical Management in Pediatric Medicine. NPJ Genom Med, 2016. 1.

Teague, B., et al. High-resolution human genome structure by single-molecule analysis. Proc Natl Acad Sci U S A, 2010. 107(24): p. 10848-53.

Travers, K.J., et al. A flexible and efficient template format for circular consensus sequencing and SNP detection. Nucleic Acids Res, 2010. 38(15): p. e159.

Valouev, A., et al. Alignment of optical maps. J Comput Biol, 2006. 13(2): p. 442-62.

Vardi Y. et al. (2000), "The multifvariate L1-median ans associated data depth," Proceedings of the national Academy of Sciences 97(4):1423-1426.

Welch, R.L., et al. Denaturation mapping of *Saccharomyces cerevisiae*. Lab Chip, 2012. 12(18): p. 3314-21.

Zhou, S., F. et al., A single molecule scaffold for the maize genome. PLoS Genet, 2009. 5(11): p. e1000711.

\* cited by examiner

SYSTEMS AND METHODS FOR IDENTIFYING SEQUENCE INFORMATION FROM SINGLE NUCLEIC ACID MOLECULE MEASUREMENTS

CROSS-REFERENCE TO RELATED APPLICATIONS

This application is related to, claims priority, and incorporates herein by reference in its entirety U.S. Provisional Patent Application No. 62/594,385, filed Dec. 4, 2017.

STATEMENT REGARDING FEDERALLY FUNDED RESEARCH

This invention was made with government support under CA182360 and HG000225 awarded by the National Institutes of Health. The government has certain rights in the invention.

BACKGROUND

Nucleic acid molecule analysis is of significant important to the biological sciences. New methods are needed to quickly and effectively analyze the underlying genomic information in nucleic acid molecules. It would be beneficial to provide methods that can analyze single nucleic acid molecules or groups of single nucleic acid molecules and provide relevant information about the underlying genomic information.

SUMMARY

In one aspect, the present disclosure provides a method of acquiring data associated with a nucleic acid molecule. The method includes the following steps: a) binding a plurality of marker molecules to at least a portion of the nucleic acid molecule, each of the plurality of marker molecules providing a detectable signal, the detectable signal including underlying genomic information about the nucleic acid molecule; b) acquiring the detectable signal from a plurality of locations along the at least a portion of the nucleic acid molecule; and c) generating an output signal or a report including the detectable signal.

In another aspect, the present disclosure provides a method of analyzing detectable signals acquired from a plurality of nucleic acid molecules. The method includes the following steps: a) receiving a data set comprising profiles of detectable signal intensity versus position, the detectable signal intensity acquired from a plurality of marker molecules bound to substantially identical portions of the plurality of nucleic acid molecules; b) extracting underlying genomic information from the data set; and c) generating an output signal or a report including the underlying genomic information.

In yet another aspect, the present disclosure provides a method including the following steps: a) binding at least a portion of each of a plurality of nucleic acid molecules with a plurality of fluorescent molecules, the plurality of fluorescent molecules providing a detectable fluorescence signal, the detectable fluorescence signal comprising underlying genomic information about a given portion of a nucleic acid molecule to which a given fluorescent molecule is bound, the at least a portion of each of the plurality of nucleic acid molecules having overlapping regions with substantially identical features; b) acquiring the detectable fluorescence signal versus position for the at least a portion of each of the plurality of nucleic acid molecules, thereby resulting in a data set comprising profiles of the detectable fluorescence signal versus position; c) identifying outliers of the profiles of the detectable signal versus position, thereby producing outlier profiles; d) computing a median profile from the profiles of the detectable signal versus position that were not identified as outlier profiles in step c); e) computing a weighted mean profile by estimating a similarity index between the profiles of the detectable signal versus position that were not identified as outlier profiles in step c) and the median profile of step d), then taking a weighted average of the profiles of the detectable signal versus position that were not identified as outlier profiles in step c) by weighting according to the similarity index, thereby producing a template; f) registering the profiles of the detectable signal versus position to the template, thereby producing registered profiles of the detectable signal versus position; g) identifying outliers of the registered profiles of the detectable signal versus position, thereby producing outlier registered profiles; h) computing a median registered profile from the registered profiles of the detectable signal versus position that were not identified as outlier registered profiles in step g); i) computing an updated weighted mean profile by estimating a registered similarity index between the registered profiles of the detectable signal versus position that were not identified as the outlier registered profiles in step g) and the median registered profile, then taking a weighted average of the registered profiles of the detectable signal versus position that were not identified as outlier registered profiles in step g) by weighting according to the registered similarity index, thereby producing a registered template; i) registering the registered profiles of the detectable signal versus position to the registered template, thereby producing second registered profiles of the detectable signal versus position, the registering of step i) a lower penalty parameter than the registering of step f); j) computing an average similarity between the registered profiles of the detectable signal versus position and the registered template; k) repeat steps g), h), i), and j) using a second penalty parameter that is lower than the lower penalty parameter until a difference between the average similarity for consecutive iterations of the repeating is lower than a threshold value, thereby producing final registered profiles of the detectable signal versus position; l) identifying outliers of the final registered profiles of the detectable signal versus position from the final iteration of step k), thereby producing outlier final registered profiles; m) computing a median final registered profile from the final registered profiles of the detectable signal versus position that were not identified as outlier final registered profiles in step l); and n) computing a final weighted mean profile by estimating a final registered similarity index between the final registered profiles of the detectable signal versus position that were not identified as the final outlier registered profiles in step l) and the median final registered profile, then taking a final weighted average of the final registered profiles of the detectable signal versus position that were not identified as outlier final registered profiles in step l) by weighting according to the final registered similarity index, thereby producing a consensus profile of the detectable signal versus position.

In a further aspect, the present disclosure provides a non-transitory computer readable medium having stored thereon instructions that, when executed by a processor, cause the processor to execute one of the methods described herein.

In yet a further aspect, the present disclosure provides a system including a processor and the non-transitory computer-readable medium described elsewhere herein.

In an additional aspect, the present disclosure provides a system including a fluorescence microscope, a processor, and a memory.

BRIEF DESCRIPTIONS OF THE DRAWINGS

DETAILED DESCRIPTION

Before the present invention is described in further detail, it is to be understood that the invention is not limited to the particular embodiments described. It is also understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices and methods relating to modifying biological molecules are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. When two or more ranges for a particular value are recited, this disclosure contemplates all combinations of the upper and lower bounds of those ranges that are not explicitly recited. For example, recitation of a value of between 1 and 10 or between 2 and 9 also contemplates a value of between 1 and 9 or between 2 and 10.

The various aspects may be described herein in terms of various functional components and processing steps. It should be appreciated that such components and steps may be realized by any number of hardware components configured to perform the specified functions.

Methods

This disclosure provides a variety of methods. It should be appreciated that various methods are suitable for use with other methods. Similarly, it should be appreciated that various methods are suitable for use with the systems described elsewhere herein. When a feature of the present disclosure is described with respect to a given method, that feature is also expressly contemplated as being useful for the other methods and systems described herein, unless the context clearly dictates otherwise.

Figure 1:
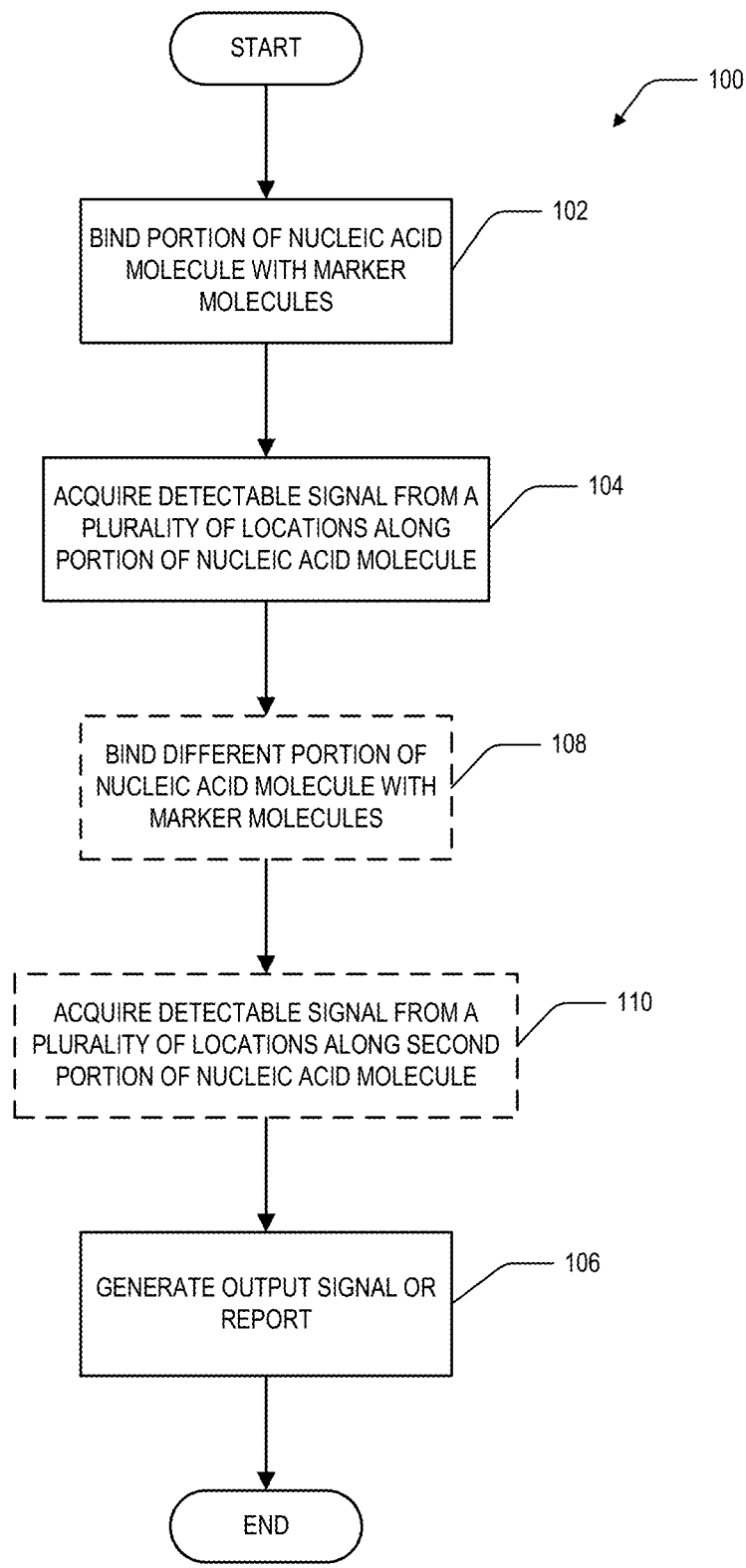
FIG. 1 is a flowchart showing the steps of a method, in accordance with an aspect of the present disclosure.

Referring to FIG. 1, the present disclosure provides a method 100 of acquiring data associated with a nucleic acid molecule. At process block 102, the method 100 includes binding at least a portion of the nucleic acid molecule with a plurality of marker molecules. Each of the plurality of marker molecules provides a detectable signal that includes underlying genomic information about the nucleic acid molecule. At process block 104, the method 100 includes acquiring the detectable signal from a plurality of locations along the at least a portion of the nucleic acid molecule. At process block 106, the method 100 can include generating an output signal or a report including the detectable signal.

At optional process block 108, the method 100 can include binding at least a second portion of the nucleic acid molecule with a second plurality of marker molecules. Each of the second plurality of marker molecules provide the detectable signal. At optional process block 110, the method 100 can include receiving the detectable signal at a second plurality of locations along the at least a second portion of the nucleic acid molecule.

In some cases, the method 100 can include repeating process blocks 102 and 104 a second time replacing the nucleic acid molecule with a second nucleic acid molecule. The nucleic acid molecule and the second nucleic acid molecule can have substantially the same sequence. The nucleic acid molecule and the second nucleic acid molecule can have different sequences. As used herein, "substantially the same sequence" refers to nucleic acid sequences that are indistinguishable using the methods of the present disclosure. Nucleic acid molecules having substantially the same sequence can harbor the following differences: (a) single nucleotide polymorphisms (SNPs) or single nucleotide variations (SNVs)—a single basepair difference in sequence; (2) small insertions and delections (INDELs)—short 1-100 bp insertions or deletions; and (3) methylations, such as C-me and A-me. As used herein, "different sequence" refers to nucleic acid sequences that are distinguishable using the methods of the present disclosure.

In some cases, the method 100 can include repeating process blocks 102 and 104 a plurality of additional times replacing the nucleic acid molecule with a different one of a plurality of additional nucleic acid molecules each of the plurality of additional times. The nucleic acid molecule and the plurality of additional nucleic acid molecules can have substantially the same sequence. The at least a portion of the nucleic acid molecule and the at least a portion of the different one of the plurality of additional nucleic acid molecules can at least partially overlap.

Figure 2:
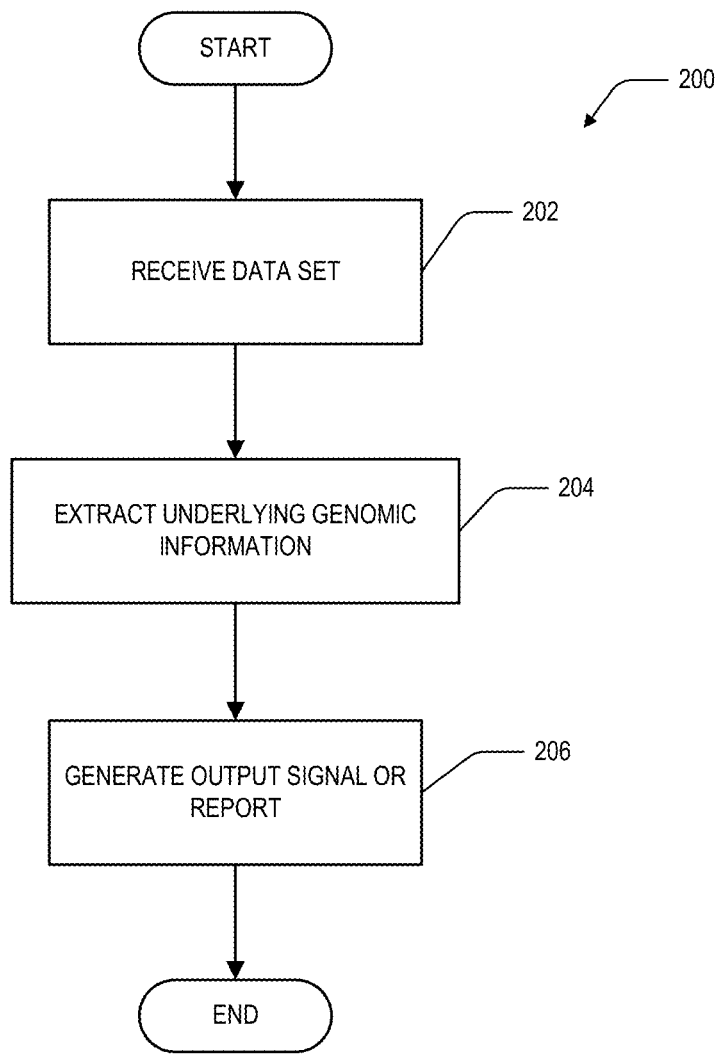
FIG. 2 is a flowchart showing the steps of a method, in accordance with an aspect of the present disclosure.

Referring to FIG. 2, the present disclosure provides a method 200 of analyzing detectable signals acquired from a plurality of nucleic acid molecules. At process block 202, the method 200 includes receiving a data set. The data set includes profiles of detectable signal intensity versus position. The detectable signal intensity is acquired from a plurality of marker molecules bound to substantially identical portions of the plurality of nucleic acid molecules. At process block 204, the method 200 includes extracting underlying genomic information from the data set. At process block 206, the method 200 includes generating an output signal or a report including the underlying genomic information.

In any of the methods, the detectable signal can contain the underlying genomic information as a result of the marker molecules preferentially binding to one sequence relative to another. For example, a marker molecule or fluorescent molecule that preferentially binds to GC-rich segments relative to AT-rich segments can provide information regarding the amount of GC versus AT in the underlying genomic information.

The plurality of marker molecules can comprise a plurality of fluorescent molecules. In cases involving fluorescent molecules, the fluorescent molecule can be a fluorescent molecule capable of binding a nucleic acid molecule, including but not limited to, {1,1'-(4,4,8,8-tetramethyl-4,8-diazaundecamethylene)bis[4-[(3-methylbenzo-1,3-oxazol-2-yl)methylidene]-1,4-dihydroquinolinium] tetraiodide} (YOYO-1) ethidium bromide, oxazole yellow (YOYO fluor monomer), SYTOX Orange, SYTOX green, SYBR gold, YO-Pro-1, POPO-3, DAPI, or the like.

The plurality of marker molecules can include a plurality of first fluorescent molecules and plurality of second fluorescent molecules. The plurality of marker molecules can also include a plurality of third fluorescent molecules, a plurality of fourth fluorescent molecules, a plurality of fifth fluorescent molecules, and so on, up to a plurality of nth fluorescent molecules. Each of these different fluorescent molecules can interact with one another to provide the detectable signal. Each of these different fluorescent molecules can have different emission characteristics, such as emission wavelength, emission waveform, and the like. Each of these different fluorescent molecules can have different absorption characteristics, such as absorption wavelength, absorption coefficient, and the like. Each of these different fluorescent molecules can have different binding characteristics.

The methods described herein can also include binding any of the nucleic acid molecules or at least a portion of any of the nucleic acid molecules with a plurality of quencher molecules. The quencher molecules can modulate emission from the plurality of marker molecules to provide the detectable signal.

The plurality of marker molecules can include a plurality of donor molecules and a plurality of acceptor molecules. The plurality of marker molecules can include a plurality of protein markers, including intercalating fluorescent proteins, such as those described in Lee, S., Oh, Y., Lee, J., Choe, S., Lim, S., Lee, H. S., . . . Schwartz, D. C. (2016). DNA binding fluorescent proteins for the direct visualization of large DNA molecules. *Nucleic Acids Research*, 44(1), e6. doi:10.1093/nar/gkv834, the entire contents of which are incorporated herein by reference.

Figure 3:
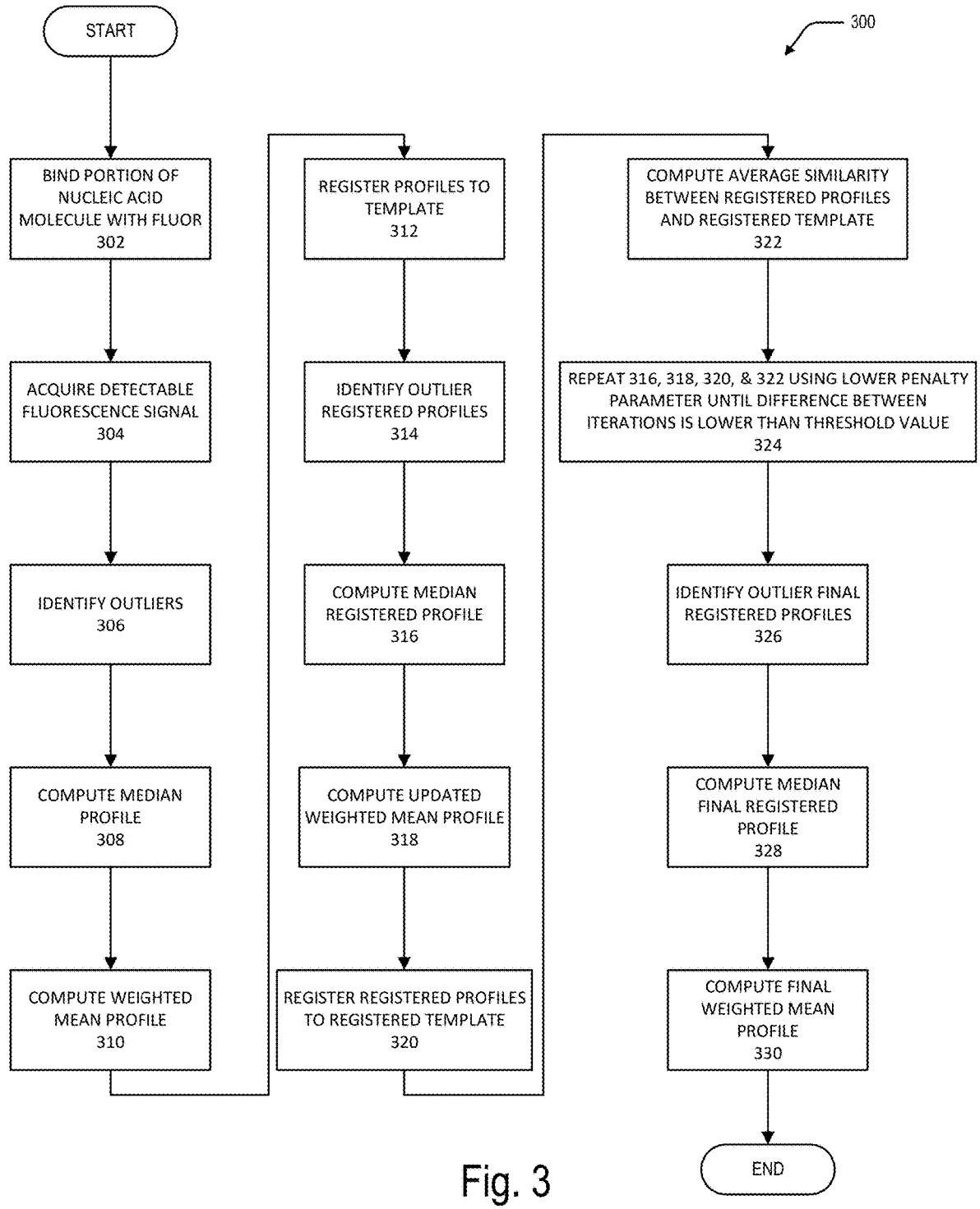
FIG. 3 is a flowchart showing the steps of a method, in accordance with an aspect of the present disclosure.

Referring to FIG. 3, the present disclosure provides a method 300. The method 300 is one specific implementation of a combination of methods 100 and 200. The description of method 300 should not be interpreted as limiting the interpretation of the methods 100 and 200. Aspects of the method 300 can utilize aspects of the methods 100 and 200 and vice versa. At process block 302, the method 300 includes binding at least a portion of each of a plurality of nucleic acid molecules with a plurality of fluorescent molecules. It should be appreciated that the exemplary fluorescent molecules are merely one example of the marker molecules described above and other marker molecules are contemplated. The plurality of fluorescent molecules provide a detectable fluorescence signal that includes underlying genomic information about a given portion of a nucleic acid molecule to which a given fluorescent molecule is bound. The at least a portion of each of the plurality of nucleic acid molecules have overlapping regions with substantially identical features.

At process block 304, the method 300 includes acquiring the detectable fluorescence signal versus position for the at least a portion of each of the plurality of nucleic acid molecules. The acquiring of process block 304 results in a data set including profiles of the detectable fluorescence signal versus position.

At process block 306, the method 300 includes identifying outliers of the profiles of the detectable signal versus position, thereby producing outlier profiles. A person having ordinary skill in the imaging arts would appreciate a variety of methods exist for eliminating images of poor quality. In one non-limiting example, a sophisticated image quality assessment method was developed, to identify high quality images for subsequent analysis. This image quality assessment method includes the following steps: 1. For each molecule in an image frame we analyzed the integrated fluorescence intensity measurements (IFI) of up to three pixels surrounding the molecule. 2. Bayesian Information Criteria (BIC) and Gaussian mixture model (GMM) to cluster the IFI's. In good quality molecule images had one cluster of IFI's. 3. In case of multiple clusters, distance between the centers of farthest centroids of clusters was used as one of the factors to build the quality score. The other factors were cluster quality measures such as Dunn index and Connectivity Index (see Brock, Guy, Vasyl Pihur, Susmita Datta, Somnath Datta, et al. 2011. clvalid, an r package for cluster validation. *Journal of Statistical Software* (Brock et al., March 2008), the entire contents of which are incorporated herein by reference). 4. A training set of 300 images was manually labeled as "high" and "low" quality. A logistic regression model was fit using the factors described in step (3). 5. Using cross-validation an optimal probability cutoff was obtained, to detect an image as "high" quality by minimizing type-II error.

Additional data processing can be performed. For instance, the profiles can be normalized. As another example, the profiles can be selected to ensure that data for DNA molecules fall within a given range of stretch values (such as +/-10% of the median stretch). AS yet another example, the scans can be smoothed using methods known to those having ordinary skill in the art, such as B-spline De Boor (De Boor, Carl. 1978. *A practical guide to splines*, vol. 27. Springer-Verlag New York, the entire contents of which are incorporated herein by reference) smoothing methods. Some pre-processing steps are described in greater detail below in Example 1.

At process block 308, the method 300 includes computing a median profile from the profiles of the detectable signal versus position that were not identified as outlier profiles in process block 306. The median profile can be computed using functional data depth measures that are understood to those having ordinary skill in the art, including but not limited to, the Fraiman and Muniz depth, the h-modal depth, the random projection depth, the random Tukey depth, and the like.

At process block 310, the method 300 includes computing a weighted mean profile, thereby producing a template including the weighted mean profile. The weighted mean profile is computed by estimating a similarity index between the profiles of the detectable signal versus position that were not identified as outlier profiles in process block 306 and the median profile of process block 308, then taking a weighted average of the profiles of the detectable signal versus position that were not identified as outlier profiles in process block 306 by weighting according to the similarity index.

At process block 312, the method 300 includes registering the profiles of the detectable signal versus position to the template, thereby producing registered profiles of the detectable signal versus position. In some cases, the registering of process block 312 can include curve registration, described as follows. Let n functions (or curves) $f_1, \ldots, f_n$ be defined on a close real interval [0,S]. Let $h_i(x)$ be a transformation of the abscissa x for curve i. Without amplitude noise, let the observed functions $f_i(x)$ be a result of warping a true curve $f_c(x)$ as $f_i(x)=f_c[h_i(x)]$. The warping function is often referred to as 'time warping' as time is a common abscissa in problems with phase noise, In the context of the present disclosure, the abscissa is DNA molecule backbone. The warping functions should satisfy the following:

$h_i(0)=0$ and $h_i(S)=S$, $i=1, \ldots, n$,

The timings of events remain in the same order regardless of the timescale entails that $h_i$, the time-warping function, should be strictly increasing, i.e., $h_i(x_1) > h_i(x_2)$ for $x_1 > x_2$, where $x_1, x_2 \in [0,S]$.

$h_i^{-1}=[h_i(x)]=1, \ldots, n$

The objective of curve registration is that the registered functions $f_1(h_1^{-1}(x)), \ldots, f_n(h_n^{-1}(x))$ will have no phase noise.

At process block 314, the method 300 includes identifying outliers of the registered profiles of the detectable signal versus position, thereby producing outlier registered profiles. Identifying outliers of the registered profiles can include functional data depth measures. Examples of suitable functional data depth measures include, but are not limited to, the Fraiman and Muniz depth, the h-modal depth, the random projection depth, the random Tukey depth, and the like.

Depth and outlyingness are inverse notions, so that if an outlier is in the data set, the corresponding curve will have a significantly low depth. One exemplary procedure for functional outlier detection in a data set of curves $f_1, \ldots, f_n$ is as follows:

1. Obtain the function depths $D_n(f_1), \ldots, D_n(f_n)$, (This could be any depth defined above: FMD, MD, RPD or RTD)
2. Let $f_{i1}, \ldots, f_{ik}$ be the k curves such that $D_n(f_{ik}) \leq C$, for a given cutoff C. Then assume that $f_{i1}, \ldots, f_{ik}$ are outliers and delete them from sample.
3. Then, come back step 1 with the new data set after deleting the outliers found in step 2. Repeat this until no mere outliers found.

To ensure type-I error of detecting outliers is under some small threshold a, C is chosen such that $$\mathbb{P}_{(D_n)}(f_i) \leq C) = \alpha, i=1, \ldots, n$$

However, since the distribution of the functional depth statistics are usually unknown, they are estimated using a bootstrap procedure introduced in Febrero et al. (Febrero, Manuel, Pedro Galeano, and Wenceslao González-Manteiga. 2008. Outlier detection in functional data by depth measures, with application to identify abnormal nox levels. *Environmetrics* 19(4):331-345, the entire contents of which are incorporated herein by reference) and implemented in R-packagefda.usc (Febrero-Bande, M, and M Oviedo de la Fuente. 2012a. fda.usc: Functional data analysis and utilities for statistical computing (fda.usc). *R package version* 0.9 7, and Febrero-Bande, Manuel, and Manuel Oviedo de la Fuente. 2012b. Statistical computing in functional data analysis: the r package fda. usc. *Journal of Statistical Software* 51(4):1-28, the entire contents of both are incorporated herein by reference). The smoothed bootstrap procedure based on trimming runs as follows:

Obtain the functional depths $D_n(f_1), \ldots, D_n(f_n)$, for any one of the functional depths.

Obtain B standard bootstrap samples of size n from the data set of curves obtained after deleting the $\alpha\%$ least deepest curves. The bootstrap samples are denoted by $f_i^b$, for $i=1, \ldots, n$ and $b=1 \ldots, B$.

3. For each bootstrap set $b=1, \ldots, B$, obtain $C^b$ as the empirical 1% percentile of the distribution of the depths, $D(f_i^b)$.
4. Take C as the median of the values of $C^b$, $b=1, \ldots, B$.

The level $\alpha$ used can be chosen as the proportion of suspicious outliers in the sample. In the Fscan data sets, $\alpha=0.15$ since around 15% of images were expected to have unusable intensity profiles, based on quality score measurement.

Selecting a function data depth measure can be done by simulating noisy curves and outliers and selecting the measure that best identifies outliers. In some cases, the functional data depth measure can be a combination of FM-depth and RP-depth, as discussed below.

At process block 316, the method 300 includes computing a median registered profile from the registered profiles of the detectable signal versus position that were not identified as outlier registered profiles in process block 314. The computing of process block 316 can be achieved by the same or similar methods as described above with respect to the computing of process block 308.

At process block 318, the method 300 includes computing an updated weighted mean profile, thereby producing a registered template including the weighted mean profile. The updated weighted mean profile is computed by estimating a registered similarity index between the registered profiles of the detectable signal versus position that were not identified as the outlier registered profiles of process block 314 and the median registered profile, then taking a weighted average of the registered profiles of the detectable signal versus position that were not identified as outlier registered profiles in process block 314 by weighting according to the registered similarity index. The computing of process block 318 can be achieved by the same or similar methods as described above with respect to the computing of process block 310.

At process block 320, the method 300 includes registering the registered profiles of the detectable signal versus position to the registered template, thereby producing second registered profiles of the detectable signal versus position. The registering of process block 320 can be achieved by the same or similar methods as described above with respect to the registering of process block 312. The registering of process block 320 has a lower penalty parameter than the registering of process block 312.

At process block 322, the method 300 includes computing an average similarity between the registered profiles of the detectable signal versus position and the registered template. The computing of process block 322 can be achieved using the same or similar methods as described below with respect to the PRIMR algorithm.

At process block 324, the method 300 includes repeating process blocks 316, 318, 320, and 322 using a second penalty parameter that is lower than the lower penalty parameter. The repeating of process block 300 continues until a difference between the average similarities for consecutive iterations of the repeating is lower than a threshold value. The products of the repeating of process block 300 are the final registered profiles.

At process block 326, the method 300 includes identifying outliers of final registered profiles of the detectable signal versus position from the final iteration of process block 324, thereby producing outlier final registered profiles. The identifying of process block 326 can be achieved using the same or similar methods as described above with respect to the computing of process block 314.

At process block 328, the method 300 includes computing a median final registered profile from the final registered profiles of the detectable signal versus position that were not identified as outlier final registered profiles at process block 326.

At process block 330, the method 300 includes computing a final weighted mean profile, thereby producing a consensus profile of the detectable signal versus time. The final weighted mean profile is computed by estimating a final registered similarity index between the final registered profiles of the detectable signal versus position that were not identified as the final outlier registered profiles in process block 326 and the median final registered profile, then taking a final weighted average of the final registered profiles of the detectable signal versus position that were not identified as the final outlier registered profiles in process block 326 by weighting according to the final registered similarity index. Individual profiles are sometimes referred to as Fscans herein. The consensus profile is also sometimes referred to as a cFscan herein.

One example of the steps of process blocks 306 to 330 is the PRIMR algorithm. The PRIMR algorithm described herein iteratively uses minimum second eigenvalue method (MSEV) to register noisy Fscans. PRIMR differs from MSEV in three aspects. First, PRIMR uses outlier detection using Fraiman and Muniz (FM) depth and Random projection (RP) depth, discussed below. Second, PRIMR estimates the consensus (or average) of Fscans by first estimating an L1-Median and then estimating a weighted average of the Fscans. The L1-Median is estimating by the algorithm proposed by Vardi and Zhang in Vardi and Zhang (2000), "The multifvariate L1-median ans associated data depth," *Proceedings of the national Academy of Sciences* 97(4): 1423-1426, the entire contents of which are incorporated herein by reference, implemented in R-package robustX (Stahel, Werner, Martin Maechler, Maintainer Martin Maechler, and MASS Suggests. 2009, the entire contents of which are incorporated herein by reference) where $$\sum_{i=1}^{n} \|f_i - f_m\| \text{ where } f_i \in R^p, i = 1, \ldots, n \text{ and } \|u\| = \sqrt{\sum_{j=1}^{p} u_j^2} \quad (1)$$

Finally, in PRIMR, we use three values of the penalty parameter $\lambda$. We start at 0.001, lower it to 0.0005 after first iteration and then to 0.0001 for all subsequent iterations. $\lambda$ plays an important role in registering nearby features of the Fscans. For a higher value of $\lambda$, distant features will get registered, and for lower values of $\lambda$ only the features that are close by will be registered. The lowering of $\lambda$ in PRIMR ensures that we gradually increase our confidence in the consensus estimation.

After convergence (iteration T) the registered curves $r_1^{(T)}, \ldots, r_n^{(T)}$ are run through steps 1 and 2, to update the template one last time to $f_c^{(T+1)}(x)$ which serves as the consensus Fscan (or cFscan) of this set of Fscans. The average similarity $\bar{\rho}_{f_c,n}^{(T+1)}$ is a measure of the quality of registration. Higher values of $\bar{\rho}_{f_c,n}$ imply less noise in the registered Fscans.

Algorithm Partial Re-Weighted Iterated MSEV Registration (PRIMR) for cFscans

For any genomic interval where there are n molecular intervals aligned, let the preprocessed Fscans be represented as $f_1(x), \ldots, f_n(x)$, $x \in [1,p]$, where p denotes the stretch of the Fscans in pixels. Let the registered Fscans at iteration t be represented as $r_1^{(t)}(x), \ldots, r_n^{(t)}(x)$. At t=0, $r_i^{(0)}(x)=f_i(x)$, i=1, ..., n.

At iteration t, t≥1, do

Step 1: Outlier detection For the Fscans $r_1^{(t-1)}(x), \ldots, r_n^{(t-1)}(x)$, detect outliers using FM-depth and RP-depth and tag the union of two sets as the outliers of this set of Fscans.

Step 2: Template compute/update: When t=1, compute the template $f_c^{(1)}$. For t>1, update the template ($f_c^{(t)}$). To compute/update the template, we employ a 2-step approach. Do 1. Median: Here we ensure that the $L_1$-Median, $f_m^{(t)}$ is estimated only from the Fscans not tagged as "functional outliers" in Step 1.

2. Weighted mean: Estimate the similarity index between the Fscans and the median $\rho_i^{(t)}=\rho(r_i^{(t-1)}, f_m^{(t)}$, i=1, ..., n aid estimate the template $f_c^{(t)}$ as the weighted average of the Fscans, with the weights being these similarity indices.

$$f_c^{(t)}(x) = \frac{1}{n}\sum_{i=1}^{n} \rho_i^{(t)} \cdot r_i^{(t-1)}(x)$$

Step 3: Registration: We use the MSEV method to register the original Fscans $f_1, \ldots, f_n$ to template $f_c^{(t)}$ and obtain registered Fscans $r_1^{(t)}, \ldots, r_n^{(t)}$. The penalty parameter is $\lambda^{(0)}=0.001$, $\lambda^{(1)}=0.0005$, $\lambda^{(t)}=0.0001$ $\forall t \geq 2$.

Step 4: Convergence of iteration: The objective of iterated registration is to maximize the average similarity to the consensus $$\bar{\rho}_{f_c,n}^{(t)} = \frac{1}{n}\sum_{i=1}^{n} \rho(f_c^{(t)}, r_i^{(t)})$$

We iterate steps 1-4, until $$\left|\bar{\rho}_{f_c^{(t)},n}^{(t)} - \bar{\rho}_{f_c^{(t-1)},n}^{(t-1)}\right| < \eta$$

for some predetermined $\eta$. We use $\eta=0.001$.

Fraiman and Muniz were among the first to introduce a functional data depth. Let $F_{n,x}(f_i(x))$ be the empirical cumulative distribution function of the values of the curves $f_1(x), \ldots, f_n(x)$ at any $x \in [a,b]$, given by $$F_{n,x}(f_i(x)) = \frac{1}{n}\sum_{k=1}^{n} \mathbb{1}\{f_k(x) \leq f_i(x)\} \quad (2)$$

and, the univariate depth of a point $f_1(x)$ is given by $$D_n(f_i(x)) = 1 - \left|\frac{1}{2} - F_{n,x}(f_i(x))\right| \quad (3)$$

Then, the Fraiman and Muniz functional depth (FMD), or a curve $f_i$ with respect to the set $f_1(x), \ldots, f_n(x)$ is given by $$FMD_n(f_i) = \int_a^b D_n(f_i(x))dx \qquad (4)$$

$$= \int_a^b 1 - \left|\frac{1}{2} - F_{n,x}(f_i(x))\right|$$

Higher values of FMD implies deeper curve; lower values of FMD implies more distant from the deepest curve.

Random projection depth is based on measuring the depth of the functional data and their derivatives under projections. The basic idea is to project each curve and its first derivative along a random direction, and defining a point in $\mathbb{R}^2$. Now, a data depth in $\mathbb{R}^2$ provides an order of the projected points. Using a large number of random projects, the mean value of the depths of the projected points defines a depth for functional data. Given the set of curves $f_1, \ldots, f_n$ and a direction v that belongs to an independent direction process $$V(\cdot), = T_{i,v} = \langle v, f_i \rangle = \int_a^b v(x)f_i(x)dx.$$

Similarly, $T_{i,v}' = \langle v, f_i' \rangle$ is the project of the first derivative $f_i'(x)$ in the direction v. Therefore, the pair $(T_{i,v}, T_{v,i}')$ is a point in $\mathbb{R}^2$. Now, if $v_1, \ldots, v_p$ are p independent random directions, then the random projection depth of a curve $f_i$ is defined as:

$$RPD_n(f_i) = \frac{1}{p}\sum_{j=1}^{p} D_n(\langle v_j, f_i \rangle) \qquad (5)$$

For example, $D_n(\bullet)$ could be modal depth in $\mathbb{R}^2$.

The method 300 can further include generating a predicted consensus profile. The predicted consensus profile can be generating by the SUBAGGING algorithm described below. The predicted consensus profile can be generated by varying the underlying predicted genomic information. The predicted genomic information can be varied to minimize the difference between the predicted consensus profile and the consensus profile. Generating the predicted consensus profile can use random forest (RF), gradient boosting (GF), or both.

In the MM Fscan datasets discussed below in Example 1, there were 30,560 intervals, each 50 pixels long, that satisfied the selection criteria of PRIMR. cFscans of all the intervals were estimated using PRIMR. For each interval, its cFscan is a smooth curve over 50 data points, each data point corresponding to the expected fluorescence intensity measurements of 206 bp of genomic subsequence. The counts of genomic elements in these 206 bp subsequences are used as features and the cFscans as the responses of the prediction models. The features were counts of nucleotides G, C, A, T's, counts of all possible 2-mers GG, GC, GA, . . . , TT's, all possible 3-mers, 4-mers and 5-mers in 206 bp subsequences. There are 16 ($4^2$) 2-mers, 64 ($4^3$) 3-mers, 256 ($4^4$) 4-mers and 1,024 ($4^5$) 5-mers. Including the counts of G, C, A, and T's this adds up to 1,364 features. Additionally, a Gaussian kernel was used along the backbone of a DNA molecule, to account for the point spread function of the emitters (fluorescent dyes intercalated with bases). Consequently, contribution from two additional 206 bp subsequences on each side of a pixel was incorporated, accounting for a total of ~1 kb genomic subsequence contributing to the integrated fluorescence intensity measurement of one pixel. The Gaussian kernel was incorporated as additional features. The total number of features was 6,820 (1,364×5). The length of the response vector was 1,528,000 pixels (30,560 intervals×50). Corresponding to a pixel point j on the cFscan the counts of k-mers in window j, along with counts of k-mers in windows j+ and j++ are used as features. Each window is of 206 bp. For example, the feature at is counts of the 2-mer "at" in corresponding windows, the feature at+ is counts of "at" in windows j+ and the feature at++ is counts of "at" in windows j++.

RF is a relatively recent tree-based machine learning tool that has enjoyed increasing popularity with the proliferation of big data analytics. Ever since its introduction (Breiman, L. 2001. Random forests. *Machine learning* 45(1):5-32, the entire contents of which are incorporated herein by reference), RF has been increasingly used in regression and classification settings (Efron, Bradley, and Trevor Hastie. 2016. *Computer age statistical inference*, vol. 5. Cambridge University Press, the entire contents of which are incorporated herein by reference). RF is particularly appealing in high-dimensional settings and in prediction involving features with multicollinearity. RF combines the concepts of adaptive nearest neighbors and bagging (Breiman, Leo. 1996. Bagging predictors. *Machine learning* 24(2):123-140, the entire contents of which are incorporated herein by reference) for effective data-adaptive prediction and inference (Chen, Xi, and Hemant Ishwaran. 2012. Random forests for genomic data analysis. *Genomics* 99(6):323-329, the entire contents of which are incorporated herein by reference). "Boosting" methods were originally used for improving performance of "weak learners" in binary classification problems Efron and Hastie (2016), by re-sampling training point, and giving more weight to the misclassified ones. Friedman in Friedman, Jerome H. 2001. Greedy function approximation: a gradient boosting machine. *Annals of statistics* 1189-1232, the entire contents of which are incorporated herein by reference, proposed "gradient boosting machine" for additive expansions based on several different fitting criteria. Boosting iteratively adds basis functions in a greedy fashion such that each additional basis function reduces the selected loss function. In the context of trees, boosting involves repeatedly growing shallow trees, each growing on the residuals of the previous tree and build up an additive model consisting of a sum of trees Efron and Hastie (2016). Balmann and Yu in Balmann Peter, and Bin Yu. 2003. Boosting with the l 2 loss: regression and classification. *Journal of the American Statistical Association* 98(462):324-339, the entire contents of which are incorporated herein by reference, investigate boosting with $L_2$ loss. We used random forest and stochastic gradient boosting assuming Gaussian distribution of the error, minimizing squared-error loss and built a prediction model between sequence compositions and cFscans.

RF models were fit using R-package "randomForest" (Liaw, Andy, and Matthew Wiener. 2002. Classification and regression by randomforest. *R news* 2(3):18-22), the entire contents of which are incorporated herein by reference. GB models were fit using R-package "gbm" (Ridgeway, Greg, et al. 2006. gbm: Generalized boosted regression models. *R package version* 1(3):55), the entire contents of which are incorporated herein by reference.

In one non-limiting example, the model in the following equation was fit:

$$h: \mathbb{R}^d \to \mathbb{R}, \text{ where, } d=6,820 \qquad (6)$$

based on the data (X,Y), where X is the d-dimensional predictor variable (genomic sequence composition counts) and Y is univariate response of length (N=1,528,000). To avoid overfitting, and to fit the models efficiently (computational efficiency) using the parallelized framework of CHTC running HTCondor 2, a Subagging algorithm was implemented (3) to fit the prediction function h. Subagging is a sobriquet for subsample aggregating, where sub-samples of the data are used instead of bootstrap for aggregation (in Bagging). Büchlmann and Yu (2002) argue in favor of subagging since it is computationally economical while still being approximately as accurate as bagging. The subagging algorithm developed for predicting pFscans is described below.

After fitting prediction models, the relative importance of features can be analyzed using methods known to those having ordinary skill in the art. For example, for RF models, the total decrease in node impurities from splitting on a features, averages over all trees, gives a notion of feature important. Node impurity can be measured by residual sum of squares. The higher decrease in node impurity of a feature, the more important it is for prediction. As another example, to estimate feature importance from GB models, the definition approximate measure of relative influence in decision trees, from Breiman, et al. (Breiman, Leo, Jerome Friedman, Charles J Stone, and Richard A Olshen. 1984. *Classification and regression trees*. CRC press, the entire contents of which are incorporated herein by reference) can be used.

Algorithm SUBAGGING for pFscan Prediction Using RF and GB

Separate the data into training (90%) ($X_r$, $Y_r$) and testing sets (10%) ($X_s$, $Y_s$)

Step 1: For k=1, . . . , K (e.g. K=1000), do

Generate a random sample ($X_r^k$, $Y_r^k$), by randomly drawing without replacement p columns and 20p rows from $X_r$. $X_r^k$:(p×20p), $Y_r^k$:(1×20p)

Compute the sub-sampled estimator using random forest, on ($X_r^k$, $Y_r^k$)

$$\hat{f}^k(\bullet): \mathbb{R}^p \to \mathbb{R}$$

Compute the sub-sampled estimator using gradient boosting, ($X_r^k$, $Y_r^k$)

$$\hat{g}^k(\bullet): \mathbb{R}^p \to \mathbb{R}$$

Step 2: Average the sub-sampled estimators to approximate $$\hat{h}(\bullet) \approx \frac{1}{K}\sum_{k=1}^{K}\frac{1}{2}\left(\hat{f}^k(\bullet) + \hat{g}^k(\bullet)\right)$$

Step 3: For prediction using sub-sampled estimators, for j=1, . . . , T, T≤K, do $\hat{Y}_{s,(f)}^j = \hat{f}^j(X_s)$ prediction using random forest only
$\hat{Y}_{s,(g)}^j = \hat{g}^j(X_s)$ prediction using gradient boosting only $$\hat{Y}_{s,(b)}^j = \frac{1}{2}\left(\hat{f}^j(X_s) + \hat{g}^j(X_s)\right)$$

prediction using both

Step 4: Average than sub-sampled predictions $$\hat{Y}_{s,(f)} = \frac{1}{T}\sum_{k=1}^{T}\hat{f}^j(X_s)$$

prediction using random forest only $$\hat{Y}_{s,(g)} = \frac{1}{T}\sum_{k=1}^{T}\hat{g}^j(X_s)$$

prediction using gradient boosting only $$\hat{Y}_{s,(b)} = \frac{1}{T}\sum_{k=1}^{T}\frac{1}{2}\left(\hat{f}^j(X_s) + \hat{g}^j(X_s)\right)$$

prediction using both

In any of the methods, any nucleic acid molecule(s) can be linearly stretched. In any of the methods, at least a portion of any of the nucleic acid molecule(s) can be confined within a nanoslit.

The binding of process block 102 or process block 302 can be via various types of bonds, including but not limited to, covalent bonds, ionic bonds, polar bonds, hydrogen bonds, or a combination thereof. The binding of process block 102 or process block 302 can involve intercalating the marker molecules between bases of the nucleic acid molecule. For example, YOYO-1 intercalates itself between DNA bases. The binding of process block 102 or process block 302 can utilize YOYO-1 or other similar dyes, as would be appreciated by a person having ordinary skill in the art.

YOYO-1 (oxazole yellow) exhibits a very large degree of fluorescence enhancement on binding to nucleic acids. Previous studies have observed a 2-fold quantum yield increase when switching from AT-rich regions to GC-rich regions. Other studies observe that fluorescence intensity depends on the base sequence. This suggests that quantum yield and fluorescence lifetime for YOYO complexed with GC-rich DNA sequences are about twice as large as those complexed with AT-rich sequences. As a result, the probability of dye molecules intercalating between DNA bases and fluorescing is non-uniform.

The detectable signals described herein can be optical signals. The optical signals can be optical fluorescence signals. The detectable signals can be initiated by an external stimulus, such as electromagnetic radiation. Detectable signals could be: (1) speech patterns or other sound waves; (2) any dynamical process evolving over time; (3) 2-D images; or other signals sharing relevant characteristics with those listed. The detectable signals can include electrical signals, such as changes in local electrical polarizability, magnetic fields (i.e., ferromagnetic nanoparticles conjugated to dyes or other binding moieties), or the like.

The receiving the detectable signal of process block 104 and/or the acquiring the detectable fluorescence signal versus position of process block 304 can include acquiring an image, such as a fluorescence image, of a nucleic acid molecule that has been bound by the marker molecules and/or the fluorescent molecule. The receiving the detectable signal of process block 104 and/or the acquiring the detectable fluorescence signal versus position of process block 304 is described at pages 1-10 of Nandi, Subrangshu (submitted 2007, publication embargoed), "Statistical Learning Methods for Fluoroscanning", doctoral dissertation, University of Wisconsin-Madison, which is incorporated herein in its entirety by reference.

One example of extracting the underlying genomic information of process block 204 can be found at pages 11-114 of Nandi, Subrangshu (submitted 2007, publication embargoed), "Statistical Learning Methods for Fluoroscanning", doctoral dissertation, University of Wisconsin-Madison, which is incorporated herein in its entirety by reference. In some cases, the extracting of process block 204 can include the same or similar steps as those described in process blocks 306 to 330.

In some cases, the extracting of process block 204 can include eliminating outliers from the data set. Eliminating outliers in process block 204 and other places described herein can use Fraiman and Muniz (FM) depth and random projection (RP) depth.

In some cases, the extracting of process block 204 can include normalizing the profiles of detectable signal intensity versus position. The extracting of process block 204 can include excluding the profiles of detectable signal intensity versus position corresponding to nucleic acid molecules that have a stretch falling outside a predetermined range of acceptable stretch values. The extracting of process block 204 can include smoothing the profiles of detectable signal intensity versus position. The smoothed profiles can be renormalized following smoothing.

The extracting of process block 204 can include generating a consensus profile of detectable signal intensity versus position. A consensus profile is also sometimes referred to as a cFscan herein. Generating the consensus profile can include correcting for amplitude variability between the profiles of detectable signal intensity versus position. Generating the consensus profile can include correcting for phase variability between the profiles of detectable signal intensity versus position.

Generating the consensus profile can include an iterated registration process. Generating the consensus can include an iterative process having the following steps: (i) detecting outliers; (ii) computing a template on a first iteration and updating the template on subsequent iterations; (iii) register the profiles of detectable signal intensity versus position to the template; and (iv) compute an average similarity between the profiles of detectable signal intensity versus position and the template, wherein the iterative process is repeated until the average similarity is maximized, the registered profiles from step (iii) of the final iteration of the iterative process are subjected to steps (i) and (ii) and the updated template of step (ii) is the consensus profile.

The methods described herein can include correlating the consensus profile to one or more features of the underlying genomic information. As used herein, a feature of the underlying genomic information can include any smallest detectable unit of underlying genomic information. In some cases, this smallest detectable unit can be a 2-mer, a 3-mer, a 4-mer, or a 5-mer.

In some cases, the extracting of process block 204 can include generating a predicted data set using predicted underlying genomic information, and minimizing a difference between the data set and the predicted data set by varying the predicted underlying genomic information, wherein the underlying genomic information is the predicted underlying genomic information that minimizes the difference.

Systems

This disclosure also provides systems. The systems can be suitable for use with the methods described herein. When a feature of the present disclosure is described with respect to a given system, that feature is also expressly contemplated as being combinable with the other systems and methods described herein, unless the context clearly dictates otherwise.

Figure 4:
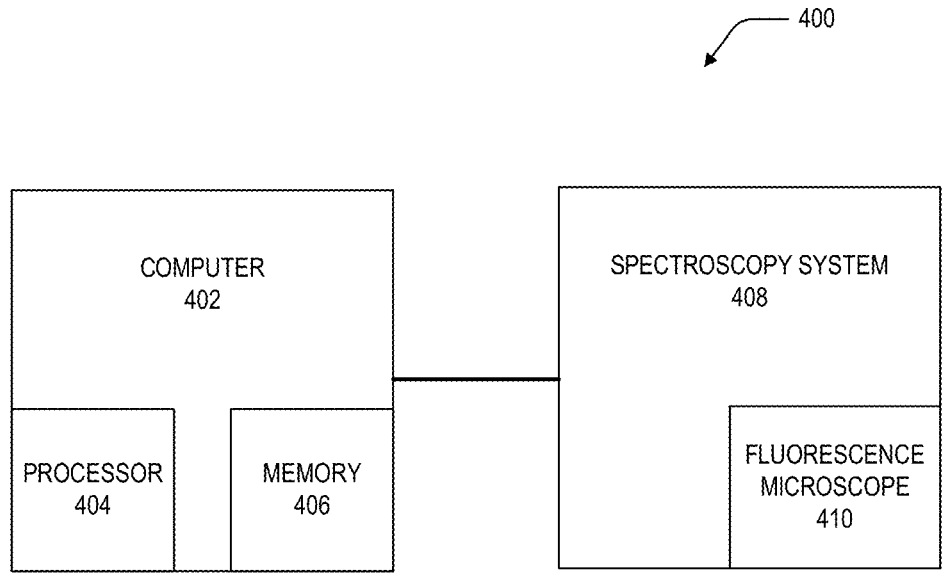
FIG. 4 is a schematic representation of a system, in accordance with an aspect of the present disclosure.

Referring to FIG. 4, a system 400 can include a computer 402 with a processor 404 and/or a CPU and a memory 406. The system 400 can also include a spectroscopy system 408. The spectroscopy system 408 can include a fluorescence microscope 410. The computer 402 can be configured to control the spectroscopy system 408 and/or the fluorescence microscope 410.

The processor 404 and/or CPU can be configured to read and perform computer-executable instructions stored in the memory 406. The computer-executable instructions can include all or portions of the methods described herein.

The memory 406 can include one or more computer readable and/or writable media, and may include, for example, a magnetic disc (e.g., a hard disk), an optical disc (e.g., a DVD, a Blu-ray, a CD), a magneto-optical disk, semiconductor memory (e.g., a non-volatile memory card, flash memory, a solid state drive, SRAM, DRAM), an EPROM, an EEPROM, and the like. The memory can store the computer-executable instructions for all or portions of the methods described herein.

EXAMPLE 1

*M. forum* are members of the class Mollicutes, a large group of bacteria that lack a cell wall and have a characteristically low GC content). These diverse organisms are parasites in a wide range of hosts, including humans, animals, insects, plants, and cells grown in tissue culture). Aside from their role as potential pathogens, *M. forum* are of interest because of their extremely small genome size. The *M. forum* genome is 793 kb.

DNA samples were prepared from purified CD138 plasma cells (MM-S and MM-R sample) and paired cultured stromal cells (normal) from a 58-year old male Multiple Myeloma (MM) patient with International Staging System (ISS) Stage IIIb disease. MM is the malignancy of B lymphocytes that terminally differentiate into longlived, antibody-producing plasma cells. Although it is a cancer genome, substantial portions of it are still identical to the reference human genome. This genome was comprehensively analyzed to characterize its structure and variation by integrating findings from optical mapping with those from DNA sequencing-based genomic analysis (see Gupta et al. (2015)).

High molecular weight DNA (500 ng) was extracted from washed cells by embedding in a 20 µl agarose gel insert; followed by dialysis in a mix comprising 10×NEB3 buffer (4.0 µl), (each, 100 µm final concentration: dATP, dCTP, dGTP and dTTP) on ice for 1 hr. Endogenous nicks were then healed by addition of: 1 µl of 10 U/µl *E. coli* ligase (10 U/µl NEB *E. coli* ligase) for 2 hrs (16° C.). Followed by addition of 1 µl of Pol I (5 U/µl Roche *E. coli* DNA Pol I nuclease free) for 4 hrs (16° C.); total volume=40 µl. Reaction was stopped by decanting solution and adding 930 µl 1×TE and 70 µl of 0.5 M EDTA (pH 8) with overnight incubation at 4° C. Solution was decanted, followed by insert dialysis steps (2×): 1 hr, against 1×TE (1.0 ml) and 0.5 M EDTA (70 µl; pH=8.0). Insert was then transferred for additional pre-treatment: 10.7 µl H2O, 4 µl NEB3 buffer, 0.8 µl (1 mM) Alexafluor 647-dUTP (20 µm final concentration; Molecular Probes) 0.8 µl (1 mM each: dATP, dCTP, dGTP; 20 µM each final concentration), and 2.7 µl dTTP (1.5 µM;

0.1 µm final concentration—placed on ice for 1 hr. Treated insert DNA was then labeled by adding 1 µl Pol I (5 U/µl); incubated at 16° C. for 1 hr; stopped with 930 µl 1×TE and 70 µl EDTA (0.5 M; pH=8.0). Nanocode labeled DNA was electroluted and diluted for imaging.

Fluorochrome-labeled nucleotides at cognate nick sites placed fluorescent tags on the genomic DNA, which were then imaged and analyzed using in-house image processing software INCA. The DNA backbones were tracked by detecting the pixel with maximum intensity in a one pixel wide vertical window of predefined size and linking these pixels via a standard shortest path algorithm. Punctate "blobs" were detected using the ratio of the eigenvalues of the local 2-by-2 Hessian matrix. The punctates were localized on the backbone using the registration information between the backbone and punctate images. The Nmaps were extracted as an ordered sequence of distances (along the backbone) between adjacent punctates. In addition to obtaining Nmaps, INCA provides the integrated fluorescence intensities of image pixels along the DNA backbone, or Fscans.

To obtain the *M. forum* dataset, single-molecule Nmaps were aligned to an in silico restriction map derived from *M. forum* reference sequence 3 and to obtain the MM dataset, single-molecule Nmaps were aligned to an in silico restriction map derived from human reference sequence (NCBI Build 37) using an in-house alignment software called Software for Optical Mapping Analysis (SOMA). SOMA grouped similar Nmaps to the genomic regions where they aligned. Single Nmaps usually have experimental errors comprising false extra cuts, false missing cuts, and sizing issues, which were modeled with different probabilistic error models.

Acquired images were processed using the image quality assessment method described above to eliminate outliers. The cross validation average type-II error was 3.52%.

Two large data-sets were prepared from samples of (1) *M. forum*, and (2) Human genome. Each dataset clearly identified groups of Fscans that aligned to the same reference intervals. While the *M. forum* Fscan data-sets provided depth (large number of Fscans aligned to the same reference interval), the human Fscan data-sets provided width (large number of intervals) but not as deep as *M. forum*.

The *M. forum* genome presents 39 intervals, which ranged in size from 2.111 kb to 81.621 kb. A *M. florum* Nmap dataset was created using previously described protocols and image analysis (see Jo, Kyubong, Dalia M Dhingra, Theo Odijk, Juan J de Pablo, Michael D Graham, Rod Runnheim, Dan Forrest, and David C Schwartz. 2007. A single-molecule barcoding system using nanoslits for dna analysis. *Proceedings of the National Academy of Sciences* 104(8): 2673-2678 and Kounovsky-Shafer, Kristy L, Juan P Hernández-Ortiz, Kyubong Jo, Theo Odijk, Juan J de Pablo, and David C Schwartz. 2013. Presentation of large dna molecules for analysis as nanoconfined dumbbells. *Macromolecules* 46(20):8356-8368, the entire contents of which are incorporated herein by reference). The reference interval lengths are calculated in image pixels: 1 pixel=209 bp of YOYO-1 stained, B-DNA at 0.34 nm/bp. Interval sizes (kb) are calculated from the Nt.BspQI in silico digest of the genome sequence.

Fluorescence intensity profiles (or Fscans) of 12 DNA molecular intervals that were aligned to interval 15 of the *M. forum* genome. The reference interval is 11.119 kb long and each pixel of the captured images correspond to 209 base pairs on the genome. So, we expect each of these Fscans to be 53 pixels long. However, due to reasons described elsewhere herein, the Fscan lengths to not perfectly math that of the reference. Table 1 shows the variability of lengths of Fscans aligned to same reference intervals. For example, in interval 19 if *M. forum* dataset, the longest Fscan is 13.6% longer and the shortest Fscan is 21.6% shorter than the average length of all Fscans aligned to that interval. Table 1 also shows the depth of *M. forum* dataset. For example, there are 1,200 Fscans for interval 7 of *M. forum*. On an average, there are 626 Fscans per *M. forum* interval. The sheer size of the *M. forum* dataset is encouraging for any statistical analysis. At the same time, it also presents unique challenges with regards to the different types of variability.

TABLE 1

Nmap Coverage of the *M. Florum* Genome

| Nt.BspQI Reference Intervals | | | *M. florum* Nmap dataset | | | |
|---|---|---|---|---|---|---|
| Interval | pixels | size (kb) | molecules | min (kb) | avg (kb) | max (kb) |
| 0 | 391 | 81.62 | 66 | 65.67 | 81.07 | 92.79 |
| 1 | 89 | 18.68 | 208 | 13.27 | 18.64 | 21.55 |
| 2 | 284 | 59.4 | 467 | 43.92 | 59.24 | 69.39 |
| 3 | 67 | 13.94 | 734 | 9.59 | 13.86 | 17.34 |
| 4 | 43 | 9.03 | 895 | 6.47 | 8.99 | 11.48 |
| 5 | 24 | 5.04 | 849 | 2.14 | 5.02 | 5.9 |
| 6 | 59 | 12.34 | 939 | 6.58 | 12.29 | 15.55 |
| 7 | 49 | 10.24 | 1200 | 6.74 | 10.2 | 12.22 |
| 8 | 72 | 15.02 | 965 | 11.13 | 15 | 19.48 |
| 9 | 122 | 25.45 | 751 | 20.52 | 25.45 | 30.91 |
| 10 | 19 | 3.89 | 784 | 2.4 | 3.9 | 4.94 |
| 11 | 100 | 20.89 | 898 | 14.35 | 20.83 | 26.42 |
| 12 | 75 | 15.57 | 883 | 9.97 | 15.43 | 19.24 |
| 13 | 49 | 10.21 | 855 | 6.21 | 9.98 | 13.72 |
| 14 | 45 | 9.47 | 731 | 6.84 | 9.19 | 12.79 |
| 15 | 53 | 11.12 | 631 | 5.69 | 10.42 | 13.94 |
| 16 | 24 | 4.99 | 203 | 1.46 | 4.24 | 7.99 |
| 17 | 66 | 13.73 | 151 | 8.29 | 12.97 | 16.76 |
| 18 | 126 | 26.28 | 377 | 21.17 | 25.66 | 31.02 |
| 19 | 183 | 38.28 | 551 | 29.91 | 38.14 | 43.33 |
| 20 | 10 | 2.11 | 488 | 1.46 | 2.14 | 3.18 |
| 21 | 148 | 31.02 | 572 | 18.48 | 31.12 | 35.62 |
| 22 | 91 | 19.1 | 712 | 14.66 | 19.12 | 24.44 |
| 23 | 17 | 3.62 | 918 | 1.04 | 3.61 | 6.37 |
| 24 | 154 | 32.19 | 947 | 25.89 | 32.24 | 37.16 |
| 25 | 198 | 41.3 | 876 | 30.39 | 41.2 | 48.77 |
| 26 | 47 | 9.76 | 824 | 4.62 | 9.74 | 13.15 |
| 27 | 78 | 16.38 | 835 | 10.5 | 16.34 | 20.35 |
| 28 | 75 | 15.69 | 666 | 11.18 | 15.96 | 18.9 |
| 29 | 30 | 6.28 | 653 | 4.07 | 5.86 | 7.36 |
| 30 | 175 | 36.5 | 881 | 29.11 | 36.34 | 42.61 |
| 31 | 88 | 18.31 | 795 | 12.95 | 18.24 | 21.9 |
| 32 | 153 | 32.07 | 668 | 25.75 | 31.81 | 38.11 |
| 33 | 100 | 20.95 | 431 | 15.15 | 20.86 | 23.97 |
| 34 | 16 | 3.28 | 334 | 1.25 | 3.03 | 4.6 |
| 35 | 68 | 14.26 | 295 | 11.32 | 14.16 | 16.37 |
| 36 | 245 | 51.31 | 191 | 36.6 | 50.81 | 59.52 |
| 37 | 77 | 15.99 | 103 | 12.06 | 15.9 | 18.12 |
| 38 | 86 | 17.88 | 68 | 15.04 | 17.68 | 20.14 |

While the *M. forum* genome only had 39 Nmap intervals, the human MM genome had thousands. Table 2.2 lists the number of intervals in each chromosome as part of the MM dataset. Each of these intervals had a minimum depth of 15 Fscans, i.e., the number of genomic DNA molecules aligned to these intervals. And, each reference interval was at least 50 pixels long (≈10.3 kb). Chromosome 1 had the largest number of intervals (1,880) and chromosome 13 had the fewest (148). In all, there were 21,972 intervals in the MM dataset. The average lengths of the intervals were 22.15 kb (std. dev. 7.911 kb), the longest being 110.60 kb (between base pairs 183,309,223 and 183,419,842 in chromosome 3) and the shortest being 14.32 kb (between base pairs 43,855, 328 and 43,869,645 in chromosome 5). The MM dataset that was analyzed covered 486.66 Mb (or 15.04%) of the human genome.

TABLE 2

Number of Intervals in MM Dataset

| Chromosome | Number of Intervals |
| --- | --- |
| chr1 | 1880 |
| chr2 | 1702 |
| chr3 | 1851 |
| chr4 | 1484 |
| chr5 | 1264 |
| chr6 | 1740 |
| chr7 | 1169 |
| chr8 | 1051 |
| chr9 | 787 |
| chr10 | 1074 |
| chr11 | 1290 |
| chr12 | 1000 |
| chr13 | 148 |
| chr14 | 796 |
| chr15 | 819 |
| chr16 | 838 |
| chr17 | 727 |
| chr18 | 826 |
| chr19 | 326 |
| chr20 | 574 |
| chr21 | 334 |
| chr22 | 292 |

The scans were subjected to the following pre-processing steps: 1. normalizing; 2. limiting stretch; and 3. smoothing.

Normalizing: The intensity values of the scans ranged between 6,000 and 20,000. Some of them are not of the best image quality. They are removed by the quality score thresholding. Then, we divide each Fscan intensity by the median value of an interval after truncating 10 pixels from either end of the Fscan intervals for excluding molecule regions surrounding labeled nick sites. By design, these regions support FRET (Fluorescence Resonance Energy Transfer) excitation of the labeled nick sites and consequently present attenuated pixel grey levels.

Limiting stretch: Images of molecules aligned to the same location on the genome were of different lengths (or stretch). We ensured uniform stretch in final Fscan data-sets by constraining Nmap alignments by length to be within +/−10% of the median stretch.

Smoothing: We used B-spline De Boor (1978) to smooth each of intensity profile individually. For Fscan f(x), with p observed points $x_i, \ldots, x_p$, we used p/3 breakpoints, with 4th order basis functions. We used generalized cross validation (GCV) measure to estimate the roughness penalty $\lambda^*$ for each Fscan f. $\lambda^* = \arg\min_x GCV(\lambda^*)$, for $e^{-5} \le e^5$. This way, we retained maximum signal-to-noise information. Smoothing serves dual purpose. First, it reduces the measurement noise at the pixels and second, it allows interpolation of Fscans at regular intervals ensuring they are all of the same length as the reference interval, in terms of pixels. After smoothing, all curves are normalized so they have a mean zero for subsequent analysis.

After preprocessing, the *M. forum* Fscans were analyzed to confirm that Fscans reflect underlying genomic sequence compositions. To do this, we first identified a set of equi-length (50 pixels) sub-Nmap-intervals from *M. forum*. There are 19 Nmap intervals in the *M. forum* genome that were at least 50 pixels long. Two separate statistical methods: one non-parametric, one parametric were employed. There were between 42 and 516 Fscans in these 19 sub-intervals, the average being 258. When two sub-intervals with different Fscan counts were compared, to reduce bias in favor of the sub-interval with more Fscans, a random matching step was added. In this step, a random set of Fscans from the sub-interval with the larger count was withdrawn to match the count of the sub-interval with the smaller count. Then pairwise tests were conducted between these two sets of same Fscan counts. For interval pairs with mismatch, random matching was repeated 50 times and the p-values were averaged.

A non-parametric permutation t-type test was conducted pairwise, to test the null hypothesis that Fscans from two distinct genomic sub-intervals were from the same distribution.

A functional Anderson-Darling test (FAD-test) was conducted pairwise on the same sub-intervals.

The p-values from both these tests are close to zero. Since FAD-Test has more power, the p-values are smaller and discernible differences between Fscans are detected. From the results of FT-Test and FAD-Test we conclude that preprocessed Fscans belonging to the same sub-intervals have higher resemblance to each other and less so with Fscans belonging to other sub-intervals. This is evidence that Fscans represent signature profiles of genomic regions.

The methods described above including the PRIMR algorithm were implemented on the acquired Fscans to produce cFscans. PRIMR successfully reduced noise in the Fscan datasets and more accurately estimated the cFscans of genomic intervals. cFscans exhibited striking similarity with GC-profiles. Using two different statistical methods it is confirmed that cFscans were strongly associated with GC-profiles, in the sense that intervals with dissimilar GC-profiles have dissimilar cFscans and intervals with similar GC-profiles have similar cFscans. This allowed us to verify the fluoroscanning hypothesis that fluorescence intensity signals were strongly associated with genomic sequence composition.

Analysis of differentially stretched Fscans of the *M. florum* datasets revealed that cFscans are reasonably robust to stretch.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

What is claimed is:

1. A method of analyzing detectable signals acquired from a plurality of nucleic acid molecules, the method comprising:
    a) receiving a data set comprising profiles of detectable signal intensity versus position, the detectable signal intensity acquired from a plurality of marker molecules bound to substantially identical portions of the plurality of nucleic acid molecules and generating a consensus profile of detectable signal intensity versus position, wherein the generating the consensus profile comprises an iterative process comprising the following steps: (i) detecting outliers; (ii) computing a template on a first iteration and updating the template on subsequent iterations; (iii) register the profiles of detectable signal intensity versus position to the template; and (iv)

compute an average similarity between the profiles of detectable signal intensity versus position and the template, wherein the iterative process is repeated until the average similarity is maximized, the registered profiles from step (iii) of the final iteration of the iterative process are subjected to steps (i) and (ii) and the updated template of step (ii) is the consensus profile;

b) extracting underlying genomic information from the data set; and c) generating an output signal or a report comprising the underlying genomic information.

2. The method of claim 1, wherein the extracting of step b) comprises eliminating outliers from the data set.

3. The method of claim 2, wherein the eliminating outliers uses Fraiman and Muniz (FM) depth and random projection (RP) depth.

4. The method of claim 1, wherein the extracting of step b) comprises normalizing the profiles of detectable signal intensity versus position.

5. The method of claim 1, wherein the extracting of step b) comprises excluding the profiles of detectable signal intensity versus position corresponding to nucleic acid molecules that have a stretch value falling outside a predetermined range of acceptable stretch values.

6. The method of claim 1, wherein the extracting of step b) comprises smoothing the profiles of detectable signal intensity versus position.

7. The method of claim 6, wherein the extracting of step b) comprises renormalizing the smoothed profiles of detectable signal intensity versus position.

8. The method of claim 1, wherein the generating the consensus profile comprises correcting for amplitude variability between the profiles of detectable signal intensity versus position.

9. The method of claim 1, wherein the generating the consensus profile comprises correcting for phase variability between the profiles of detectable signal intensity versus position.

10. The method of claim 1, wherein the generating the consensus profile comprises an iterated registration process.

11. The method of claim 1, the method further comprising correlating the consensus profile to a feature of the underlying genomic information.

12. The method of claim 1, wherein the plurality of marker molecules comprises a plurality of fluorescent molecules.

13. The method of claim 12, wherein the plurality of marker molecules comprises a plurality of {1,1'-(4,4,8,8-tetramethyl-4,8-diazaundecamethylene)bis[4-[(3-methylbenzo-1,3-oxazol-2-yl)methylidene]-1,4-dihydroquinolinium] tetraiodide} (YOYO-1) molecules.

14. The method of claim 1, wherein the plurality of nucleic acid molecules is a plurality of single-stranded DNA molecules, a plurality of double-stranded DNA molecules, a plurality of single-stranded RNA molecules, or a plurality of double-stranded RNA molecules.

15. The method of claim 1, wherein the extracting of step b) comprises generating a predicted data set using predicted underlying genomic information, and minimizing a difference between the data set and the predicted data set by varying the predicted underlying genomic information, wherein the underlying genomic information is the predicted underlying genomic information that minimizes the difference.

16. The method of claim 1, wherein the data set comprising the profiles of detectable signal intensity versus position were generated by a method of acquiring data associated with a nucleic acid molecule, the method comprising:

a) binding a plurality of marker molecules to at least a portion of the nucleic acid molecule, each of the plurality of marker molecules providing a detectable signal, the detectable signal comprising underlying genomic information about the nucleic acid molecule;

b) acquiring the detectable signal from a plurality of locations on the at least a portion of the nucleic acid molecule; and c) generating an output signal or a report comprising the detectable signal.

17. A method of analyzing detectable signals acquired from a plurality of nucleic acid molecules, the method comprising:

a) receiving a data set comprising profiles of detectable signal intensity versus position, the detectable signal intensity acquired from a plurality of marker molecules bound to substantially identical portions of the plurality of nucleic acid molecules;

b) extracting underlying genomic information from the data set, the extracting comprising generating a predicted data set using predicted underlying genomic information, and minimizing a difference between the data set and the predicted data set by varying the predicted underlying genomic information, wherein the underlying genomic information is the predicted underlying genomic information that minimizes the difference; and c) generating an output signal or a report comprising the underlying genomic information.

18. A method of analyzing detectable signals acquired from a plurality of nucleic acid molecules, the method comprising:

a) receiving a data set comprising profiles of detectable signal intensity versus position, the detectable signal intensity acquired from a plurality of marker molecules bound to substantially identical portions of the plurality of nucleic acid molecules, wherein the data set comprising the profiles of detectable signal intensity versus position were generated by a method of acquiring data associated with a nucleic acid molecule, the method comprising:

i) binding a plurality of marker molecules to at least a portion of the nucleic acid molecule, each of the plurality of marker molecules providing a detectable signal, the detectable signal comprising underlying genomic information about the nucleic acid molecule;

ii) acquiring the detectable signal from a plurality of locations on the at least a portion of the nucleic acid molecule; and iii) generating an output signal or a report comprising the detectable signal;

b) extracting underlying genomic information from the data set; and c) generating an output signal or a report comprising the underlying genomic information.

19. The method of claim 17, wherein the extracting of step b) comprises eliminating outliers from the data set.

20. The method of claim 17, wherein the eliminating outliers uses Fraiman and Muniz (FM) depth and random projection (RP) depth.

21. The method of claim 17, wherein the extracting of step b) comprises normalizing the profiles of detectable signal intensity versus position.

22. The method of claim 17, wherein the extracting of step b) comprises excluding the profiles of detectable signal intensity versus position corresponding to nucleic acid molecules that have a stretch value falling outside a predetermined range of acceptable stretch values.

23. The method of claim 17, wherein the extracting of step b) comprises smoothing the profiles of detectable signal intensity versus position.

24. The method of claim 17, wherein the extracting of step b) comprises renormalizing the smoothed profiles of detectable signal intensity versus position.

25. The method of claim 17, wherein the generating the consensus profile comprises correcting for amplitude variability between the profiles of detectable signal intensity versus position.

26. The method of claim 17, wherein the generating the consensus profile comprises correcting for phase variability between the profiles of detectable signal intensity versus position.

27. The method of claim 17, wherein the generating the consensus profile comprises an iterated registration process.

28. The method of claim 17, the method further comprising correlating the consensus profile to a feature of the underlying genomic information.

29. The method of claim 17, wherein the plurality of marker molecules comprises a plurality of fluorescent molecules.

30. The method of claim 29, wherein the plurality of marker molecules comprises a plurality of {1,1'-(4,4,8,8-tetramethyl-4,8-diazaundecamethylene)bis[4-[(3-methyl-benzo-1,3-oxazol-2-yl)methylidene]-1,4-dihydroquinolinium] tetraiodide} (YOYO-1) molecules.

31. The method of claim 17, wherein the plurality of nucleic acid molecules is a plurality of single-stranded DNA molecules, a plurality of double-stranded DNA molecules, a plurality of single-stranded RNA molecules, or a plurality of double-stranded RNA molecules.

32. The method of claim 17, wherein the extracting of step b) comprises generating a predicted data set using predicted underlying genomic information, and minimizing a difference between the data set and the predicted data set by varying the predicted underlying genomic information, wherein the underlying genomic information is the predicted underlying genomic information that minimizes the difference.

33. The method of claim 17, wherein the data set comprising the profiles of detectable signal intensity versus position were generated by a method of acquiring data associated with a nucleic acid molecule, the method comprising:
 a) binding a plurality of marker molecules to at least a portion of the nucleic acid molecule, each of the plurality of marker molecules providing a detectable signal, the detectable signal comprising underlying genomic information about the nucleic acid molecule;
 b) acquiring the detectable signal from a plurality of locations on the at least a portion of the nucleic acid molecule; and
 c) generating an output signal or a report comprising the detectable signal.

34. The method of claim 18, wherein the extracting of step b) comprises eliminating outliers from the data set.

35. The method of claim 18, wherein the eliminating outliers uses Fraiman and Muniz (FM) depth and random projection (RP) depth.

36. The method of claim 18, wherein the extracting of step b) comprises normalizing the profiles of detectable signal intensity versus position.

37. The method of claim 18, wherein the extracting of step b) comprises excluding the profiles of detectable signal intensity versus position corresponding to nucleic acid molecules that have a stretch value falling outside a predetermined range of acceptable stretch values.

38. The method of claim 18, wherein the extracting of step b) comprises smoothing the profiles of detectable signal intensity versus position.

39. The method of claim 18, wherein the extracting of step b) comprises renormalizing the smoothed profiles of detectable signal intensity versus position.

40. The method of claim 18, wherein the generating the consensus profile comprises correcting for amplitude variability between the profiles of detectable signal intensity versus position.

41. The method of claim 18, wherein the generating the consensus profile comprises correcting for phase variability between the profiles of detectable signal intensity versus position.

42. The method of claim 18, wherein the generating the consensus profile comprises an iterated registration process.

43. The method of claim 18, the method further comprising correlating the consensus profile to a feature of the underlying genomic information.

44. The method of claim 18, wherein the plurality of marker molecules comprises a plurality of fluorescent molecules.

45. The method of claim 44, wherein the plurality of marker molecules comprises a plurality of {1,1'-(4,4,8,8-tetramethyl-4,8-diazaundecamethylene)bis[4-[(3-methyl-benzo-1,3-oxazol-2-yl)methylidene]-1,4-dihydroquinolinium] tetraiodide} (YOYO-1) molecules.

46. The method of claim 18, wherein the plurality of nucleic acid molecules is a plurality of single-stranded DNA molecules, a plurality of double-stranded DNA molecules, a plurality of single-stranded RNA molecules, or a plurality of double-stranded RNA molecules.

47. The method of claim 18, wherein the extracting of step b) comprises generating a predicted data set using predicted underlying genomic information, and minimizing a difference between the data set and the predicted data set by varying the predicted underlying genomic information, wherein the underlying genomic information is the predicted underlying genomic information that minimizes the difference.

48. The method of claim 18, wherein the data set comprising the profiles of detectable signal intensity versus position were generated by a method of acquiring data associated with a nucleic acid molecule, the method comprising:
 a) binding a plurality of marker molecules to at least a portion of the nucleic acid molecule, each of the plurality of marker molecules providing a detectable signal, the detectable signal comprising underlying genomic information about the nucleic acid molecule;
 b) acquiring the detectable signal from a plurality of locations on the at least a portion of the nucleic acid molecule; and
 c) generating an output signal or a report comprising the detectable signal.

* * * * *

UNITED STATES PATENT AND TRADEMARK OFFICE
CERTIFICATE OF CORRECTION

| | |
|---|---|
| PATENT NO. | : 11,808,701 B2 |
| APPLICATION NO. | : 16/769883 |
| DATED | : November 7, 2023 |
| INVENTOR(S) | : David Charles Schwartz et al. |

It is certified that error appears in the above-identified patent and that said Letters Patent is hereby corrected as shown below:

In the Specification

Column 10, Line 19, "aid" should be --and--.

Column 11, Line 25, "$\int_a^b$" should be --$\int\limits_a^b$--.

Column 12, Line 51, "Balmann and Yu in Balmann" should be --Bühlmann and Yu in Bülhmann--.

Column 13, Line 60, "$\hat{Y}_{s,(f)}^j = f(X_s)$" should be --$\hat{Y}_{s,(f)}^j = \hat{f}^j(X_s)$--.

Column 13, Line 61, "$Y_{s,(g)}^j = g^j(X_s)$" should be --$\hat{Y}_{s,(g)}^j = \hat{g}^j(X_s)$--.

Column 16, Line 29, "*forum*" should be --*florum*--.

Column 16, Line 34, "*forum*" should be --*florum*--.

Column 16, Line 36, "*forum*" should be --*florum*--.

Column 17, Line 22, "*forum*" should be --*florum*--.

Column 17, Line 24, "*forum*" should be --*florum*--.

Column 17, Line 38, "*forum*" should be --*florum*--.

Column 17, Line 40, "*forum*" should be --*florum*--.

Signed and Sealed this
Twenty-seventh Day of February, 2024

Katherine Kelly Vidal
*Director of the United States Patent and Trademark Office*

CERTIFICATE OF CORRECTION (continued)
U.S. Pat. No. 11,808,701 B2

Column 17, Line 43, "*forum*" should be --*florum*--.

Column 17, Line 44, "*forum*" should be --*florum*--.

Column 17, Line 64, "*forum*" should be --*florum*--.

Column 18, Line 4, "*forum*" should be --*florum*--.

Column 18, Line 7, "*forum*" should be --*florum*--.

Column 18, Line 8, "*forum*" should be --*florum*--.

Column 18, Line 9, "*forum*" should be --*florum*--.

Column 18, Line 10, "*forum*" should be --*florum*--.

Column 18, Line 52, "*forum*" should be --*florum*--.

Column 19, Line 48, "minx" should be --$\min_\lambda$--.

Column 19, Line 56, "*forum*" should be --*florum*--.

Column 19, Line 59, "*forum*" should be --*florum*--.

Column 19, Line 60, "*forum*" should be --*florum*--.